United States Patent [19]

Harrison et al.

[11] 4,206,119

[45] Jun. 3, 1980

[54] 6-(1,3-DITHIOLAN-2-IMINO)PENICILLANIC ACID DERIVATIVES

[75] Inventors: Boyd L. Harrison; Joseph E. Dolfini, both of Cincinnati, Ohio

[73] Assignee: Richardson-Merrell Inc., Wilton, Conn.

[21] Appl. No.: 19,416

[22] Filed: Mar. 12, 1979

[51] Int. Cl.$^2$ ............................................. C07D 277/04
[52] U.S. Cl. ................................. 260/245.2; 424/246; 424/270
[58] Field of Search ................................. 260/306.7 C

[56] References Cited

U.S. PATENT DOCUMENTS 4,077,967   3/1978   Dolfini et al. ................. 260/306.7 C Primary Examiner—Nicholas S. Rizzo
Attorney, Agent, or Firm—William J. Stein; Eugene O. Retter; George W. Rauchfuss, Jr.

[57] ABSTRACT

Novel 6-(1,3-dithiolan-2-imino)penicillanic acid derivatives are described which are particularly useful for their antibacterial properties.

6 Claims, No Drawings

6-(1,3-DITHIOLAN-2-IMINO)PENICILLANIC ACID DERIVATIVES

DESCRIPTION

1. Technical Field

This invention relates to certain penicillin derivatives useful as antibacterial agents and to a method for their preparation.

2. Background Art

Penicillanic acid derivatives belong to a well-known family of antibiotics that have been widely used in recent years in the treatment of various infectious diseases. A number of commercially useful penicillin antibiotics have been obtained by varying the substitution at the 2-position of the penicillin nucleus and by various modifications of the side-chain substituents at the 6-position of the penicillin nucleus. The search continues, however, for new compounds which possess a broad spectrum of antibacterial activity and which possess a high degree of activity toward both gram-positive and gram-negative bacteria without causing undesirable contraindications when administered to humans.

In an effort to improve the properties of existing compounds, efforts have been directed towards the insertion of a 1,3-dithiolane ring onto the 6-amino group of the penicillin nucleus to produce compounds having useful antibacterial activity. More particularly, the preparation of penicillanic acid derivatives having a 1,3-dithiolan-2-imino moiety located at the 6-position of the penicillin nucleus provides novel penicillin derivatives that are effective against one or more gram-positive and gram-negative microorganisms. Accordingly, the compounds of the present invention are effective in the treatment of various infectious diseases caused by such gram-positive and gram-negative bacteria in poultry or in mammals, including man. The compounds disclosed herein are also suitable for use in certain topical germicidal preparations or as surface disinfectants.

SUMMARY OF THE INVENTION

In accordance with the present invention certain novel 6-(1,3-dithiolan-2-imino) derivatives of penicillanic acid, its salts and esters are described, which are useful for their antibacterial properties. More particularly, the present invention relates to 6-(1,3-dithiolan-2-imino)penicillanic acid derivatives having the formula

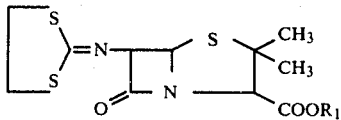

(I)

wherein $R_1$ is selected from the group consisting of hydrogen, t-butyl, 2,2,2-trichloroethyl, benzhydryl, formyloxymethyl and alkanoyloxymethyl in which the alkanoyl group contains from 2 to 5 carbon atoms; and the pharmaceutically acceptable salts thereof.

Another aspect of the present invention relates to the preparation of these novel 6-(1,3-dithiolan-2-imino)-penicillanic acid derivatives by condensing an S-alkylated salt of 1,3-dithiolane-2-thione in solution with a 6-aminopenicillanic acid having the formula

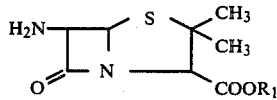

(II)

wherein the symbol $R_1$ is as previously defined. This process is of particular advantage in that it provides, for the first time, a convenient method for the direct insertion of the 1,3-dithiolan-2-imino moiety at the 6-position of the penicillin nucleus.

DETAILED DESCRIPTION OF THE INVENTION

The compounds contemplated within the scope of this invention include the compound 6-(1,3-dithiolan-2-imino)penicillanic acid, its pharmaceutically acceptable salts and certain esters thereof, as indicated by the symbol $R_1$. When the symbol $R_1$ represents hydrogen, the compound 6-(1,3-dithiolan-2-imino)penicillanic acid is delineated.

The pharmaceutically acceptable salts include the non-toxic, carboxylic acid salts that are formed with any suitable inorganic or organic base. Illustratively, these salts include those of alkali metals, as for example, sodium and potassium alkaline earth metals, such as barium, calcium and magnesium; light metals of Group III A including aluminum; and organic primary, secondary and tertiary amines including triethylamine, procaine, dibenzylamine, vinylamine, N,N'-dibenzylethylenediamine, dihydroabietylamine, N-(lower)alkylpiperidine and various other amines that have been used to form non-toxic salts of antibiotics such as benzylpenicillin. These salts are prepared via conventional methods known to those skilled in the art, as for example by the neutralization of a solution of the free carboxylic acid in a polar solvent using a stoichiometric quantity of base, and recovering the salt therefrom.

The preferred esters of 6-(1,3-dithiolan-2-imino)-penicillanic acid include the t-butyl, 2,2,2-trichloroethyl, benzhydryl, formyloxymethyl and alkanoyloxymethyl groups. The term alkanoyl as used in this regard includes those groups having a total of from 2 to 5 carbon atoms, as for example, the acetyl, propionyl, butyryl, isobutyryl, 2-methylbutyryl, 3-methylbutyryl and 2,2-dimethylpropionyl groups. In general, these ester groups confer improved absorption properties upon the molecule, while remaining physiologically labile. Such esters are readily absorbed from the gastrointestinal tract, thereby promoting oral activity. Upon absorption they are enzymatically hydrolyzed to the generally more active 6-(1,3-dithiolan-2-imino)penicillanic acid.

Illustrative specific base compounds encompassed by formula (I) above include:
6-(1,3-dithiolan-2-imino)pencillanic acid,
t-butyl 6-(1,3-dithiolan-2-imino)penicillanate,
2,2,2-trichloroethyl 6-(1,3-dithiolan-2-imino)penicillanate,
benzhydryl 6-(1,3-dithiolan-2-imino)penicillanate,
formyloxymethyl 6-(1,3-dithiolan-2-imino)penicillanate,
acetyloxymethyl 6-(1,3-dithiolan-2-imino)penicillanate,
propionyloxymethyl 6-(1,3-dithiolan-2-imino)penicillanate,
butyryloxymethyl 6-(1,3-dithiolan-2-imino)penicillanate, isobutyryloxymethyl 6-(1,3-dithiolan-2-imino)penicillanate,
2-methylbutyryloxymethyl 6-(1,3-dithiolan-2-imino)-penicillanate,
3-methylbutyryloxymethyl 6-(1,3-dithiolan-2-imino)-penicillanate,
2,2-dimethylpropionyloxymethyl 6-(1,3-dithiolan-2-imino)pencillanate, The compounds represented by claim 1 are readily prepared in good yield by condensing an S-alkylated salt of 1,3-dithiolane-2-thione (III) with a 6-amino penicillanic acid. This reaction sequence is indicated as follows wherein the symbol $R_1$ is as previously defined and the symbol X represents a halogen atom selected from the group consisting of chlorine, bromine and iodine.

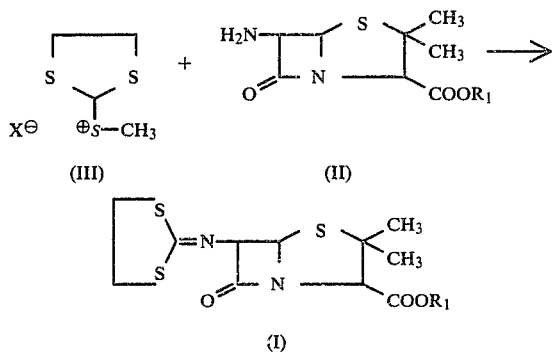

The S-alkylated salts of 1,3-dithiolane-2-thione are readily prepared by the alkylation of 1,3-dithiolane-2-thione, which is known commercially as ethylenetrithiocarbonate. Thus, for example, the addition of a methyl halide with stirring to a solution of 1,3-dithiolane-2-thione at a temperature ranging from 0° to about 50° C. for a period of from 1 to 24 hours results in the formation of the corresponding S-methyl halide salt of 1,3-dithiolane-2-thione as a crystalline salt. The S-methyl iodide salt of 1,3-dithiolane-2-thione is the alkylated salt of choice and is prepared by the addition of methyl iodide to a solution of 1,3-dithiolane-2-thione. Preferably, the reaction is conducted via the dropwise addition of methyl iodide to a nitromethane solution of 1,3-dithiolane-2-thione at room temperature under an inert atmosphere such as nitrogen or argon.

The compound 6-aminopenicillanic acid is a well-known intermediate that is used in the manufacture of synthetic penicillins. It can be isolated from fermentation broths prepared without the use of added precursers, such as phenylacetic acid, using suitable penicillin-producing molds, as for example *Penicillium chrysogenum*. The esters described herein are readily prepared from 6-aminopenicillanic acid using methods well-known to those versed in the art. Thus, for example, procedures analogous to those described by Binderup et al., Journal of Antibiotics, 24, 767 (1971), for the preparation of the corresponding cephalosporanic acid esters can be gainfully employed.

The various 6-aminopenicillanic acid derivatives (II) can be condensed as their free acids to form 6-(1,3-dithiolan-2-imino)penicillanic acid. Preferably, however, they are condensed in the form of their salts or esters. Suitable salts include the sodium and trialkylamine salts, in which the alkyl group contains from 1 to 5 carbon atoms. Suitable esters include those described herein as well as any of the silyl esters disclosed in U.S. Pat. No. 3,249,622. The condensed esters are readily isolated, and particularly in the case of the silyl esters, are readily cleaved to yield 6-(1,3-dithiolan-2-imino)penicillanic acid.

In general, the condensation of the 6-aminopenicillanic acid derivatives (II) and the S-alkylated salts of 1,3-dithiolan-2-thione (III) is conducted in the presence of a suitable solvent at temperatures ranging from −30° C. to 100° C. The reaction time varies from 15 minutes to as long as 36 hours depending upon the particular reaction temperature employed. For convenience, the reaction is preferably conducted at room temperature or slightly below for a period of from 1 to 8 hours.

Suitable solvents in which the condensation takes place include acetone, acetonitrile, dioxane, dimethylformamide, chloroform, ethylene chloride, dichloromethane and tetrahydrofuran with acetonitrile being the particular solvent of choice. In certain instances, as when the 6-aminopenicillanic acid is present in the form of its salts, mixtures of water and a miscible organic solvent may be advantageously employed. Optionally, the condensation can be conducted in the presence of an inert atmosphere, as for example argon or nitrogen gas. An excess of the S-alkylated salt of 1,3-dithiolane-2-thione (III) is also favorably employed to insure completeness of the reaction and to favor the yield of desired product obtained.

Following completion of the condensation reaction, the reaction mixture is quenched in water and the desired 6-(1,3-dithiolan-2-imino)penicillanic acid derivatives isolated via standard procedures known to those versed in the art. Thus, for example, the quenched reaction mixture is extracted with a suitable organic solvent, such as chloroform, methylene chloride or ether, the organic extract is washed with a dilute aqueous acid solution to remove any unreacted starting material, the washed organic extract is dried, concentrated and the desired 6-(1,3-dithiolan-2-imino)penicillanic acid derivatives recovered therefrom. Purification of the products is generally effected by recrystallization from chloroform or from a chloroform ether mixture.

When the 6-aminopenicillanic acid is employed, the use of a silylating agent is advantageously employed. Under these circumstances, condensation best proceeds under anhydrous conditions in anhydrous solvents. The various silylating agents employed form labile silyl esters with 6-aminopenicillanic acid and are readily soluble in anhydrous solvents. Inasmuch as these silyl esters are highly sensitive to moisture, once condensation has taken place, the esters are readily hydrolyzed to the free acid by quenching the reaction mixture in water. Suitable silylating agents that may be favorably employed include various alkyl chlorosilanes, alkyl disilazanes, alkyl silylamines and alkyl silylamides, as for example triethyl chlorosilane, tri-n-butyl chlorosilazane, dimethylethyl chlorosilane, phenylethylmethyl chlorosilane, triphenyl chlorosilane, tetraethyldimethyl disilazane, hexamethyl disilazane, tetramethyldiphenyl disilazane, hexaphenyl disilazane, N-ethyl triethyl silylamine, triphenyl silylamine, N-trimethylsilylacetamide, with the silylating agent of choice being O,N-bis-trimethylsilylacetamide.

In general, the 6-aminopenicillanic acid is suspended in a suitable anhydrous solvent, as for example acetonitrile, tetrahydrofuran or dioxane. Two equivalents of the silylating agent are added to this suspension and stirring is continued until esterification and solution occur, generally in about two hours or less at room temperature. An additional 10% excess of the silylating agent is added to insure complete esterification of the 6-aminopenicillanic acid employed. Condensation with an S-alkylated salt of 1,3-dithiolane-2-thione and the subsequent isolation of the desired product remain essentially as previously described.

The novel compounds of the present invention are useful antimicrobial agents having a broad spectrum of antimicrobial activity in vitro against standard laboratory microorganisms that are routinely used to demonstrate activity against pathogenic bacteria. The antibacterial spectrum of typical compounds described herein is determined in a standard manner by means of a qualitative diffusion assay as illustrated in Example below. The in vitro antibacterial activity of the novel compounds of this invention not only makes them useful as pharmacological agents per se, but makes them useful as additives for animal feeds, as well as additives for materials which are subject to microbial deteriorization, such as cutting oils and fuel oils. These compounds are also useful for their antibacterial effect in soaps, shampoos and in topical compositions for the treatment of wounds and burns.

The invention described herein is more particularly illustrated in conjunction with the following specific examples.

EXAMPLE 1

S-Methyl 1,3-dithiolane-2-thione iodide 1,3-Dithiolane-2-thione, (ethylenetrithiocarbonate) 13.6 g, is dissolved in 25 ml of reagent nitromethane and treated at room temperature with 14.2 g of methyl iodide via dropwise addition with stirring under an atmosphere of nitrogen. The reaction mixture is wrapped with foil for light protection and stirring continued overnight. The crystals that form are filtered, washed with dry benzene and dried in vacuo to yield 20.9 g of brown colored, crystalline S-methyl 1,3-dithiolane-2-thione iodide having a m.p.t. of 80°–3° C.

EXAMPLE 2

6-(1,3-Dithiolan-2-imino)penicillanic acid

The compound 6-aminopenicillanic acid 9.2 g, is suspended in 200 ml of dry acetonitrile and treated with 11.6 ml of bis-trimethylsilylacetamide at room temperature. Stirring is continued for 1.5 hours, at which point solution is complete, and 6.4 ml of triethylamine are added thereto. The compound S-methyl 1,3-dithiolane-2-thione, 13.9 g, is added to the silyl ester solution over a 30 minute period and stirring is continued for an additional 1.5 hours. The reaction mixture is filtered, and the filtrate quenched in 500 ml of water. The resulting aqueous mixture is extracted with chloroform, the chloroform extracts are combined, washed with dilute 0.05 N hydrochloric acid, dried over anhydrous MgSO$_4$ and evaporated to dryness in vacuo to yield 6.5 g of an orange colored residue. This residue is recrystallized several times from an acetone/ether solution using charcoal to yield approximately 1.4 g of purified 6-(1,3-dithiolan-2-imino)penicillanic acid as a white crystalline material having a m.p.t. of 160°–5° C. (dec.).

EXAMPLE 3

Benzhydryl 6-(1,3-dithiolan-2-imino)penicillanate

The compound 6-(1,3-dithiolan-2-imino)penicillanic acid, 6.4 g, prepared in accordance with the procedure of the preceding Example, is suspended in 300 ml of tetrahydrofuran and treated with 4.07 g of diphenyldiazomethane. The light purple-red reaction mixture is evaporated in vacuo to yield 7.6 g of a pink residue. Recrystallization of this residue twice from an acetone/hexane solution yields a white crystalline compound identified as benzhydryl 6-(1,3-dithiolan-2-imino)penicillanate and having a m.p.t. of 37°–9° C.

EXAMPLE 4

Pivaloyloxymethyl 6-(1,3-dithiolan-2-imino)penicillanate

The 2,2-dimethylpropionyloxymethyl ester of the hydrochloride salt of 6-aminopenicillanic acid, or pivaloyloxymethyl 6-aminopenicillanate hydrochloride, 0.05 mole, is suspended in 100 ml of anhydrous acetonitrile containing 0.15 m of triethylamine with stirring. The compound S-methyl 1,3-dithiolane-2-thione iodide, 0.055 mole, prepared in accordance with Example 1, is added with continued stirring. The reaction mixture is stirred for an additional 16 hours at room temperature, quenched in 200 ml of water and extracted with chloroform. The combined chloroform extracts are washed with a dilute 0.1 N solution of hydrochloric acid, dried over anhydrous MgSO$_4$, filtered and concentrated to dryness in vacuo. Crystallization of this residue from an acetone/hexane solution yields the desired pivaloyloxymethyl 6-(1,3-dithiolan-2-imino)penicillanate.

Following essentially the same procedure but substituting formyloxymethyl 6-aminopenicillanate hydrochloride and acetoxymethyl 6-aminopenicillanate hydrochloride for the pivaloyloxymethyl 6-aminopenicillanate hydrochloride above results in the formation of formyloxymethyl 6-(1,3-dithiolan-2-imino)penicillanate and acetoxymethyl 6-(1,3-dithiolan-2-imino)penicillanate, respectively.

EXAMPLE 5

6-(1,3-Dithiolan-2-imino)penicillanic acid

Triethylamine, 5 ml, and 6-aminopenicillanic acid, 2.14 g., are dissolved at room temperature in 20 ml of sieve-dried dimethylformamide under an atmosphere of argon gas. To this solution is added 3.06 g of S-methyl 1,3-dithiolane-2-thione iodide in portions. The reaction mixture is stirred at room temperature for a period of 2 hours and quenched into 150 ml of water. The quenched reaction mixture is extracted with four 50 ml portions of methylene dichloride followed by an additional extraction with a 100 ml portion of diethyl ether. The aqueous solution is adjusted to a pH of 2.5 using a 1 N solution of hydrochloric acid and extracted with three 100 ml portions of chloroform. The combined chloroform extracts are washed with a saturated NaCl solution, dried over anhydrous MgSO$_4$ and evaporated to dryness in vacuo to a solid foam. Trituration of this foam with diethyl ether yields the 6-(1,3-dithiolan-2-imino)penicillanic acid of Example 2.

EXAMPLE 6

The following example illustrates the in vitro activity of the compounds of this invention.

Trypticase soy broth is inoculated from a slant culture of the test bacterium the day prior to testing. The inoculated broth is incubated for 24 hours at 37° C. and 0.05 ml of the inoculated and incubated broth is added to 25 ml of melted (45°–50° C.) trypticase soy agar. The seeded agar is poured into a 100 mm square petri dish and allowed to solidify.

Approximately 1 to 3 mg of purified 6-(1,3-dithiolan-2-imino)pencillanic acid is placed directly upon the agar and the agar plate incubated overnight. Chloramphenicol is similarly applied to seeded agar as a reference standard and incubated overnight. The agar plates are examined for clear zones of bacterial growth inhibition. The diameter of each zone is measured and recorded.

The following table summarizes the various zones of inhibition expressed in millimeters observed for the various test organisms.

| Organism | 6-(1,3-dithiolan-2-imino)penicil-lanic acid (mm) | chloramphen-icol (mm) |
| --- | --- | --- |
| Staphylococcus aureus | 15 | 29 |
| Streptococcus pyogenes | 19 | 40 |
| Streptococcus faecalis | 9 | 39 |
| Salmonella schottmuelleri | 8 | 39 |
| Proteus mirabilis | 9 | 35 |
| Pseudomanas aeruginosa | 3 | 26 |
| Escherichia coli | 40 | 52 |

We claim:

1. A 6-(1,3-dithiolan-2-imino)penicillanic acid derivative having the formula

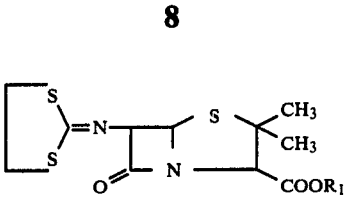

wherein $R_1$ is selected from the group consisting of hydrogen, t-butyl, 2,2,2-trichloroethyl, benzhydryl, formyloxymethyl and alkanoyloxymethyl in which the alkanoyl group contains from 2 to 5 carbon atoms; and the pharmaceutically acceptable salts thereof.

2. A compound according to claim 1 wherein $R_1$ is hydrogen.

3. A compound according to claim 1 which is 6-(1,3-dithiolan-2-imino)penicillanic acid.

4. A compound according to claim 1 which is benzhydryl 6-(1,3-dithiolan-2-imino)penicillanate.

5. A process for the preparation of a 6-(1,3-dithiolan-2-imino)penicillanic acid derivative of claim 1 which comprises condensing in solution an S-alkylated salt of 1,3-dithiolane-2-thione with a 6-aminopenicillanic acid having the formula

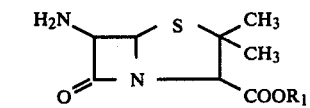

wherein the symbol $R_1$ is defined as in claim 1, and recovering the penicillanic acid derivative therefrom.

6. A process for the preparation of 6-(1,3-dithiolan-2-imino)penicillanic acid according to claim 1, which comprises condensing in solution an S-alkylated salt of 1,3-dithiolan-2-thione with a silyl ester of 6-aminopenicillanic acid, hydrolyzing the condensed silyl ester, and recovering the 6-(1,3-dithiolan-2-imino)-penicillanic acid therefrom.

* * * * *